US012350020B2

(12) United States Patent
Cohen

(10) Patent No.: US 12,350,020 B2
(45) Date of Patent: Jul. 8, 2025

(54) MULTI-PARAMETER MONITORING DEVICE

(71) Applicant: AliveCor, Inc., Mountain View, CA (US)

(72) Inventor: Sean Cohen, Mountain View, CA (US)

(73) Assignee: ALIVECOR, INC., Mountain View, CA (US)

( * ) Notice: Subject to any disclaimer, the term of this patent is extended or adjusted under 35 U.S.C. 154(b) by 368 days.

(21) Appl. No.: 17/881,278

(22) Filed: Aug. 4, 2022

(65) Prior Publication Data

US 2024/0041331 A1 Feb. 8, 2024

(51) Int. Cl.
*A61B 5/0205* (2006.01)
*A61B 5/00* (2006.01)
*G16H 10/60* (2018.01)

(52) U.S. Cl.
CPC .......... *A61B 5/0205* (2013.01); *A61B 5/0006* (2013.01); *A61B 5/681* (2013.01); *A61B 5/743* (2013.01); *G16H 10/60* (2018.01)

(58) Field of Classification Search
CPC .............................. A61B 5/0205; G16H 10/60
USPC ......................................................... 600/301
See application file for complete search history.

(56) References Cited

U.S. PATENT DOCUMENTS

| | | | |
|---|---|---|---|
| 2005/0261598 A1* | 11/2005 | Banet ................... | A61B 5/0205 600/513 |
| 2006/0009698 A1* | 1/2006 | Banet ...................... | A61B 5/26 128/903 |

\* cited by examiner

*Primary Examiner* — Nadia A Mahmood
(74) *Attorney, Agent, or Firm* — WOMBLE BOND DICKINSON (US) LLP

(57) ABSTRACT

Embodiments of the present disclosure provide a monitoring device that combines blood pressure, SpO2, and ECG monitoring functionality into a single handheld device and can measure these parameters simultaneously. The monitoring device may comprise a first sensor comprising an electrode to measure electrical signals corresponding to cardiac activity of a user's heart and a second sensor comprising an electrode as well as an optical sensor to perform a PPG and measure an amount of light absorbed by the blood of the user concurrently with measurement of the electrical signals. The optical sensor may generate a blood pressure signal and an oxygen saturation signal based at least in part on the amount of light absorbed by the blood of the user. The optical sensor may include a neural network trained to estimate blood pressure based on PPG measurements and demographic information of the user, as discussed in further detail herein.

22 Claims, 12 Drawing Sheets

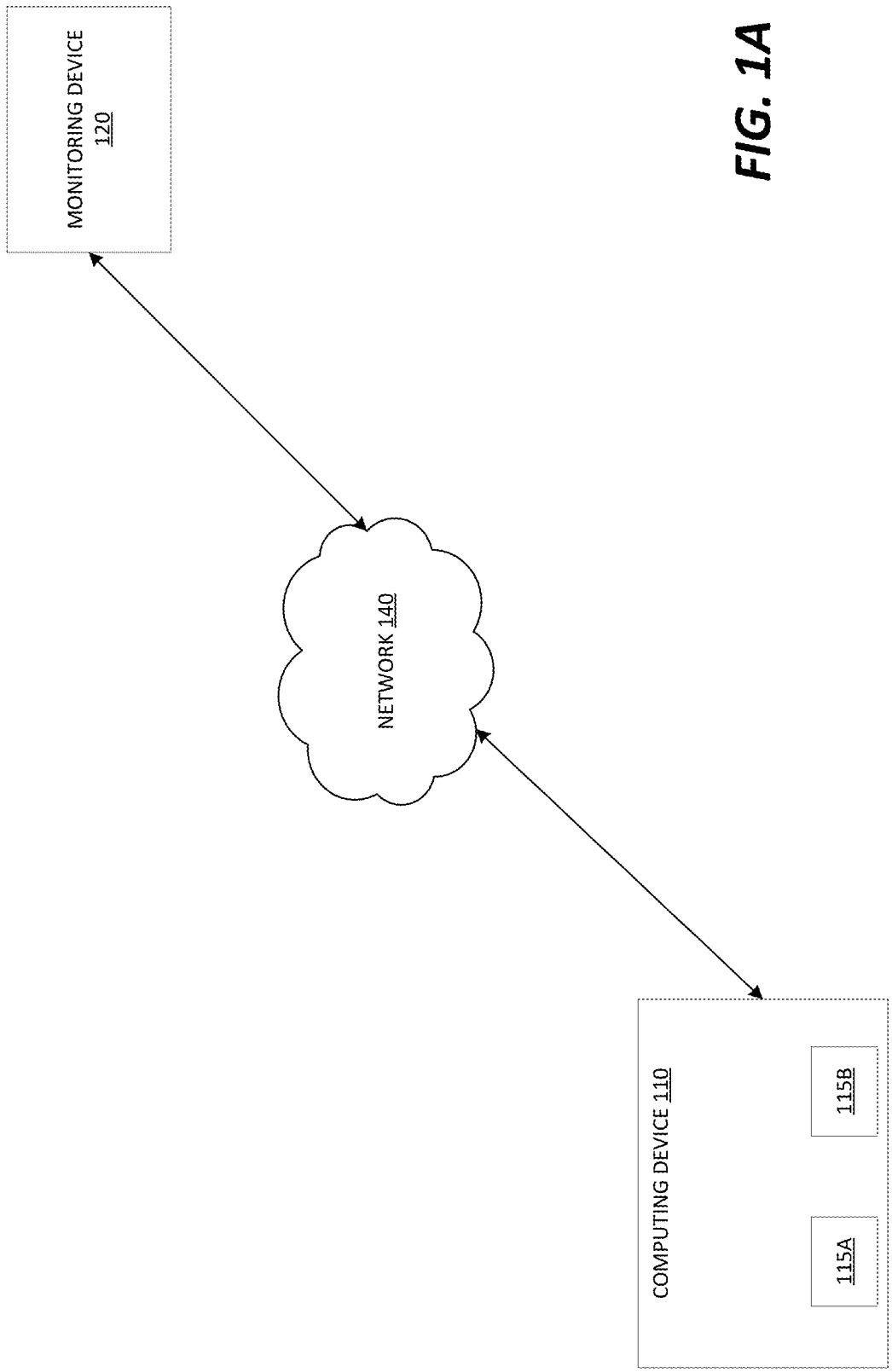

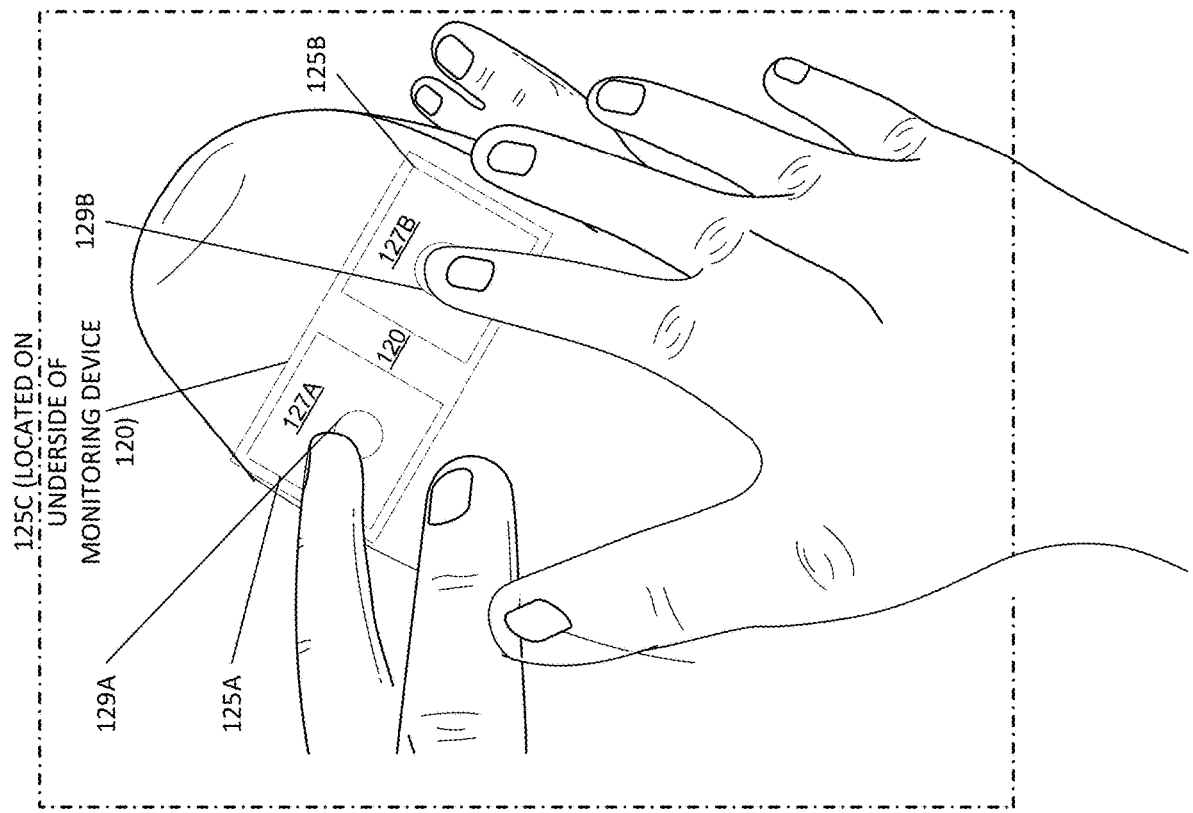

MULTI-PARAMETER MONITORING
DEVICE

TECHNICAL FIELD

The present disclosure relates to medical devices, systems, and methods and in particular, to a monitoring device that can monitor multiple physiological parameters.

BACKGROUND

Cardiovascular diseases are the leading cause of death in the world. In 2008, 30% of all global death could be attributed to cardiovascular diseases. It is also estimated that by 2030, over 23 million people will die from cardiovascular diseases annually. Cardiovascular diseases are prevalent across populations of first and third world countries alike, and affect people regardless of socioeconomic status. There are a number of key vital signs that physicians can monitor in order to determine when a person is experiencing (or will experience) a cardiac condition. One such key vital sign is the electrical activity of a subject's heart, as cardiac status and cardiac events (e.g., cardiac arrhythmia) of the subject can be tracked by monitoring the electrical activity of the subject's heart. For example, arrhythmia is a cardiac condition in which the electrical activity of the heart is irregular or is faster (tachycardia) or slower (bradycardia) than normal. An electrocardiogram (ECG) provides a number of ECG waveforms that represent the electrical activity of a person's heart. There are a number of ECG devices which can provide ECG monitoring on an ad-hoc basis to continuously monitor the electrical activity of a user's cardiovascular system. The American Heart Association and the European Society of Cardiology recommends that a 12-lead ECG should be acquired as early as possible for people with possible heart conditions when symptoms present. Prehospital ECG has been found to significantly reduce time-to-treatment and shows better survival rates.

Blood pressure is another key vital sign monitored by physicians. Blood pressure is used for the diagnosis of many medical conditions, and by itself is monitored as a key metric for the management of disease. The standard measure of blood pressure is the auscultatory method, wherein a specialist inflates a cuff around the arm and uses a stethoscope to determine the systolic blood pressure and the diastolic blood pressure. Hypertension, an elevation in either the systolic or diastolic blood pressure, is a medical condition that afflicts some 70 million Americans, and it is estimated that only about half of these people have their hypertension under control. Another key vital sign monitored by physicians is oxygen saturation (also referred to herein as blood oxygen level), which is the fraction of oxygen-saturated hemoglobin relative to total hemoglobin (unsaturated+saturated) in the blood. Blood oxygen levels that are too low (e.g., below 80%) may compromise the functioning of organs, such as the brain and heart, and continued low oxygen levels may lead to respiratory or cardiac arrest.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 1A illustrates a system, in accordance with some embodiments of the present disclosure.

FIG. 2D illustrates a monitoring device that includes functionality for measuring blood pressure, SpO2, and ECG simultaneously in operation, in accordance with some embodiments of the present disclosure.

DETAILED DESCRIPTION

It is to be understood that the present disclosure is not limited in its application to the details of construction, experiments, exemplary data, and/or the arrangement of the components set forth in the following description. The embodiments of the present disclosure are capable of other embodiments or of being practiced or carried out in various ways. Also, it is to be understood that the terminology employed herein is for purpose of description and should not be regarded as limiting.

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

An ECG monitoring device may comprise a set of electrodes for recording ECG waveforms (also referred to herein as "taking an ECG") of the person's heart. The set of electrodes may be placed on the skin of the person in multiple locations and the electrical signal recorded between each electrode pair (ECG waveform) in the set of electrodes may be referred to as a lead. The ECG waveforms (each one corresponding to a lead of the ECG) recorded by the ECG monitoring device may comprise data corresponding to the electrical activity of the person's heart. Varying numbers of leads can be used to take an ECG, and different numbers and combinations of electrodes can be used to form the various leads. Example numbers of leads used for taking ECGs are 1, 2, 6, and 12 leads.

A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 1B:
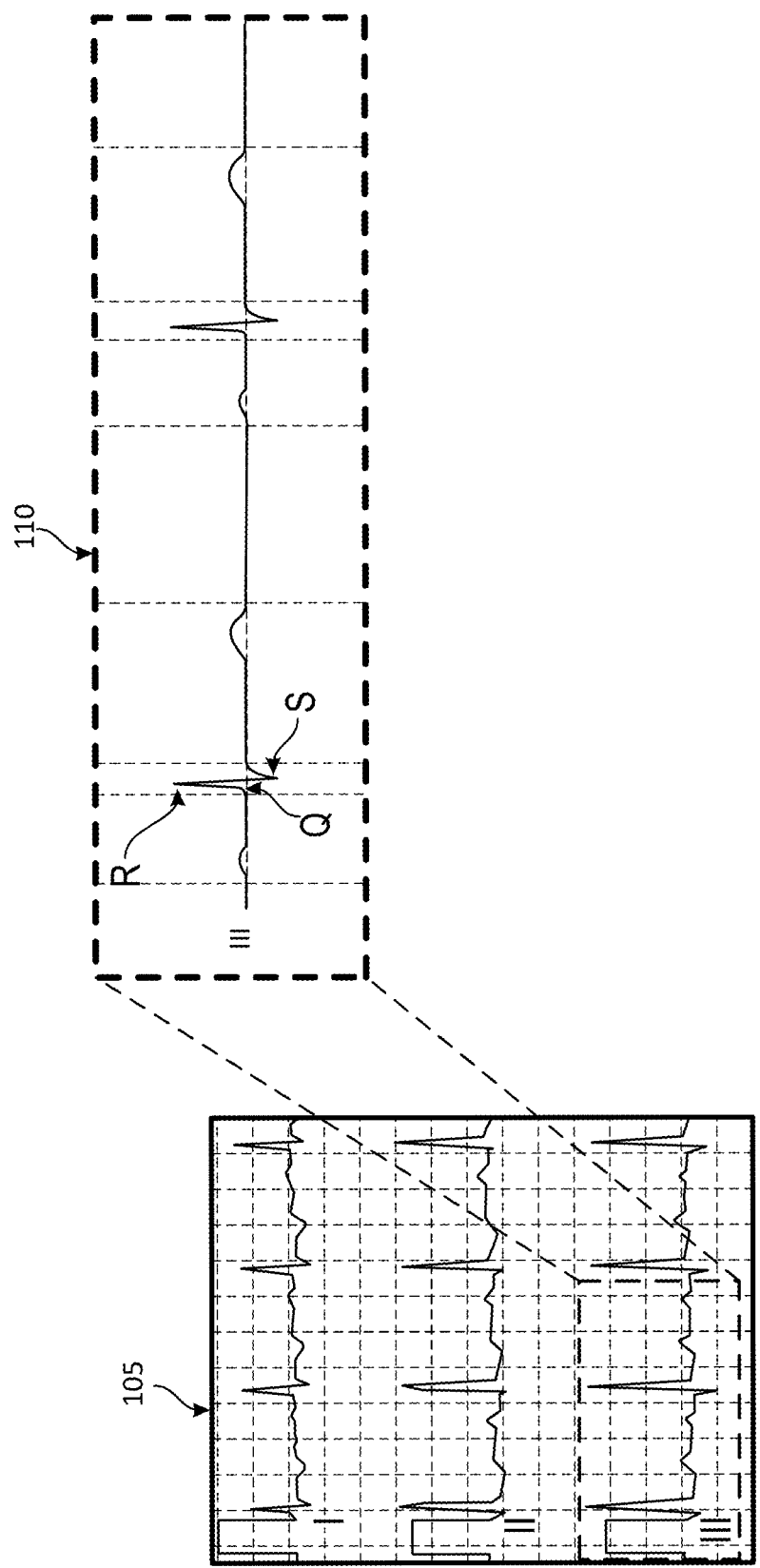
FIG. 1B is a diagram illustrating electrocardiogram (ECG) waveforms, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). This is because although the various leads may analyze the same electrical events, each one may do so from a different angle. FIG. 1B illustrates a view 105 of an ECG waveform detected by each of 3 leads (I, II, and III) when a 3-lead ECG is taken as well as an exploded view 110 of the ECG waveform measured by lead III illustrating the QRS complex. As shown, the amplitudes and morphologies of the ECG waveform taken from leads I-III are all different, with the ECG waveform measured by lead III having the largest amplitude and the ECG waveform measured by lead I having the smallest amplitude.

There are different "standard" configurations for electrode placement that can be used to place electrodes on the person. For example, an electrode placed on the right arm can be referred to as RA. The electrode placed on the left arm can be referred to as LA. The RA and LA electrodes may be placed at the same location on the left and right arms, preferably near the wrist in some embodiments. The leg electrodes can be referred to as RL for the right leg and LL for the left leg. The RL and LL electrodes may be placed on the same location for the left and right legs, preferably near the ankle in some embodiments. Lead I is typically the voltage between the left arm (LA) and right arm (RA), e.g. I=LA-RA. Lead II is typically the voltage between the left leg (LL) and right arm (RA), e.g. II=LL-RA. Lead III is the typically voltage between the left leg (LL) and left arm (LA), e.g. III=LL-LA. Augmented limb leads can also be determined from RA, RL, LL, and LA. The augmented vector right (aVR) lead is equal to RA-(LA+LL)/2 or -(I+II)/2. The augmented vector left (aVL) lead is equal to LA-(RA+LL)/2 or I-II/2. The augmented vector foot (aVF) lead is equal to LL-(RA+LA)/2 or II-I/2.

A photoplethysmogram (PPG) is a technique that detects changes in blood volume during a cardiac cycle by illuminating the skin, and measuring changes in light absorption. With each cardiac cycle the heart pumps blood (referred to as a pressure pulse) to the periphery, and the change in volume caused by the pressure pulse is detected by illuminating the skin with the light from a light source (e.g., light-emitting diodes (LEDs)) and then measuring the amount of light either transmitted or reflected using a light detector (e.g., a photodiode). The PPG has become a popular method for measuring oxygen saturation and even blood pressure and one device that is commonly used for taking a PPG is a pulse oximeter. However, a PPG can be taken using other devices as well. For example, a PPG can be performed using a mobile phone's embedded flash as a light source and the camera as a light detector when held adjacent a peripheral site such as the finger. The PPG measurement can also be made at other peripheral sites such as the ear, forehead, or chest. The PPG signal obtained consists of pulses that reflect the change in vascular blood volume with each cardiac beat.

A raw PPG signal generally includes pulsatile and non-pulsatile components, and the pulsatile component of a PPG signal is related to changes in blood volume inside the arteries and is synchronous with the heartbeat. Because the volume and distension of the arteries can be related to the pressure in the arteries, various features of a PPG waveform from a single PPG measurement may be used to effect blood pressure measurement. Features of the PPG waveform commonly used to estimate blood pressure include the amplitude, frequency, slope, area under the curve, key points along the PPG curve, and derivatives of the PPG waveform Some blood pressure measurement techniques involve the use of a machine learning model (e.g., artificial neural network), which may be trained with labeled data to learn an association between features of a PPG waveform and blood pressure.

PPG signals may be integrated with other modalities, such as ECGs, to obtain features such as pulse wave velocity, pulse transit time (PTT), and pulse arrival time (PAT) for blood pressure measurement. For example, a blood pressure monitor may receive a first ECG reading from a set of electrodes and simultaneously receive a first PPG from e.g., a pulse oximeter. The blood pressure monitor may then receive a second ECG reading from the set of electrodes and simultaneously receive a second PPG from the pulse oximeter and generate an average ECG reading from the first and second ECG readings. The blood pressure monitor may determine a differential pulse arrival time based on the average ECG reading and the first and second PPGs and determine the blood pressure of the user based on the differential pulse arrival time. The blood pressure data recorded by the blood pressure monitor may comprise the systolic and diastolic blood pressure of the first user, for example.

Another parameter that is important to measure in order to maintain the health of a user is the saturation of peripheral oxygen (the amount of oxygen being carried in a user's blood), also referred to herein as SpO2. SpO2 indicates how effectively a user is breathing and how well blood is being transported throughout their body. The SpO2 of a user may also be measured using a PPG. When the appendage of a subject is illuminated, absorption of light at certain wavelengths differs significantly between blood loaded with oxygen and blood lacking oxygen. Oxygenated blood absorbs more infrared light and allows more red light to pass through, while deoxygenated hemoglobin allows more infrared light to pass through and absorbs more red light. The ratio between different wavelengths of detected light (e.g., red light and infrared light) is then calculated and represents the ratio of oxygenated hemoglobin to deoxygenated hemoglobin.

As discussed hereinabove, each of the blood pressure, SpO2, and ECG measurements provide information that is critical for patient care. However, current devices for measuring these parameters are either implemented separately or combine the functionality to measure only two of these parameters.

Embodiments of the present disclosure provide a monitoring device that combines blood pressure, SpO2, and ECG monitoring functionality into a single handheld device, and can measure these parameters simultaneously. The monitoring device may comprise a set of sensors, and one or more of the set of sensors may comprise an electrode to measure electrical signals corresponding to cardiac activity of a user's heart as well as an optical sensor to perform a PPG and measure an amount of light absorbed by the blood of the user. Other sensors of the set of sensors may comprise an electrode to measure electrical signals corresponding to cardiac activity of a user's heart but no optical sensor. The optical sensor(s) may generate a blood pressure signal and an oxygen saturation signal based at least in part on the amount of light absorbed by the blood of the user. The optical sensor may include a neural network trained to estimate blood pressure based on PPG measurements and demographic information of the user, as discussed in further detail herein. The device may further include a processing device operatively coupled to the set of sensors. The processing device may receive the electrical signals measured by each of the set of sensors and generate one or more electrocardiogram (ECG) waveforms based thereon while concurrently receiving the blood pressure and oxygen saturation signals from the one or more sensors that have an optical sensor and transmit the ECG waveforms, blood pressure signals, and oxygen saturation signals to a computing device for display and/or analysis. In some embodiments, the device may display the ECG waveforms, blood pressure signals, and oxygen saturation signals itself. It should be noted that although discussed herein with respect to blood pressure and SpO2, other parameters may be measured by the optical sensors as well including e.g., heart rate.

FIG. 1A illustrates a system 100 for measuring and monitoring one or more biometric or physiological parameters of a user in accordance with some embodiments of the present disclosure. The system 100 may comprise a computing device 110 and a monitoring device 120. The computing device 110 and monitoring device 120 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a WiFi™ hotspot connected with the network 140 and/or a wireless carrier system that can be implemented using various data processing equipment, communication towers (e.g. cell towers), etc. In some embodiments, the network 140 may be an L3 network. In other embodiments, the network 140 may alternatively or in combination comprise a BlueTooth connection, a low power BlueTooth connection, an NFC (near field communication) connection, a near field ultrasound communication connection, or any other appropriate connection. The network 140 may carry communications (e.g., data, message, packets, frames, etc.) between computing device 110 and the monitoring device 120. In some embodiments, the computing device 110 and the monitoring device 120 may be connected by a wired connection (not shown) such as a universal serial bus (USB) connection, a Firewire connection, a Lightning connection, or the like.

The computing device 110 may include hardware such as processing device 115A (e.g., processors, central processing units (CPUs)), memory 115B (e.g., random access memory (RAM), storage devices (e.g., hard-disk drive (HDD), solid-state drive (SSD), etc.)), a network interface configured to connect with network 140, and other hardware devices (e.g., sound card, video card, etc.). In some embodiments, the memory 115B may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. The memory may be configured for long-term storage of data and may retain data between power on/off cycles of the computing device 110. The computing device 110 may comprise any suitable type of computing device or machine that has a programmable processor including, for example, server computers, desktop computers, laptop computers, tablet computers, smartphones, set-top boxes, etc. In some examples, the computing device 110 may comprise a single machine or may include multiple interconnected machines (e.g., multiple servers configured in a cluster). The computing device 110 may further comprise other components (not shown) such as motion detection components, one or more cameras, additional displays, power supplies, fans, various I/O ports, etc.

The monitoring device 120 may include a set of sensors (shown in FIG. 2A), each of which may combine optical and biopotential sensors to measure the SpO2, ECG, and blood pressure of a user as discussed in further detail herein.

Figure 2A:
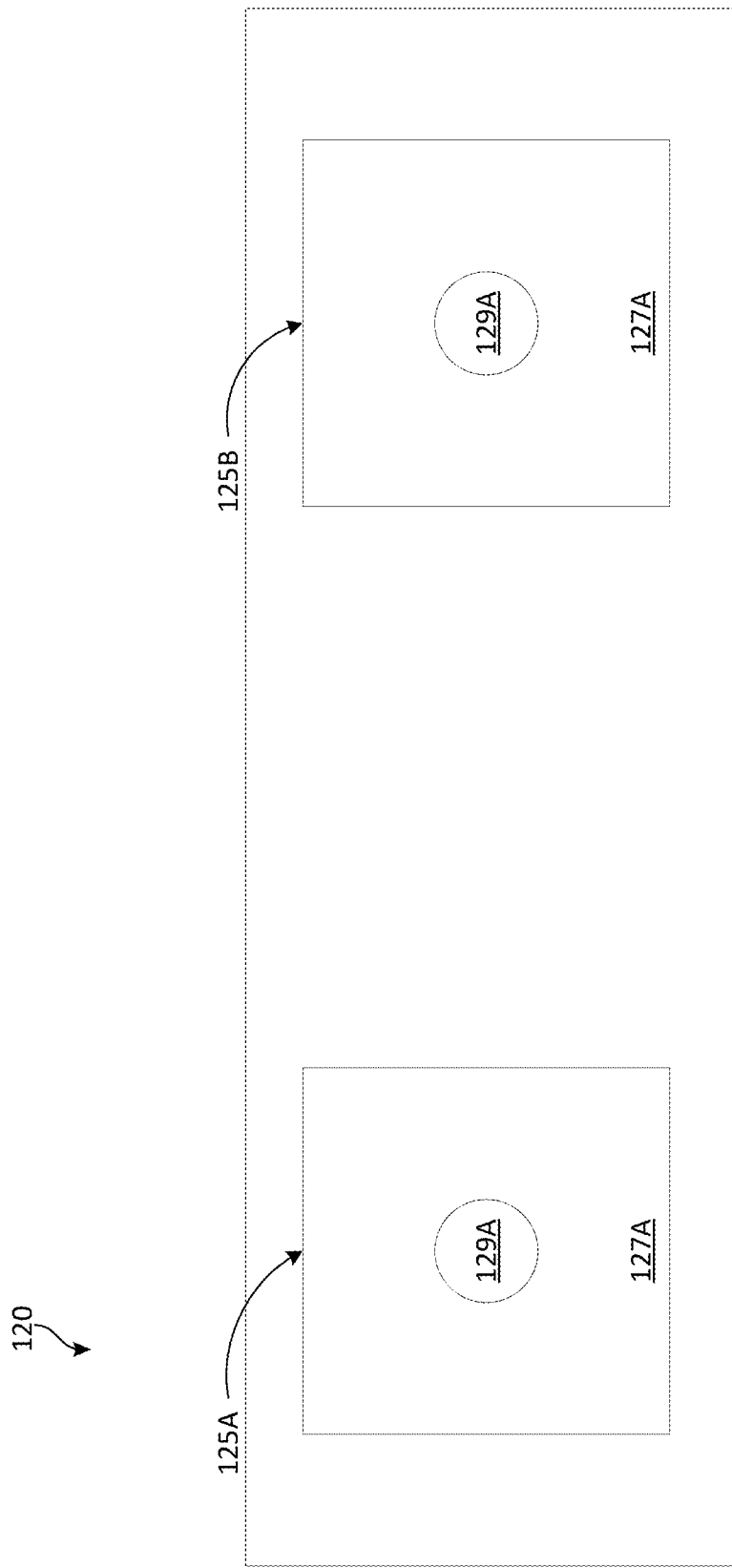
FIG. 2A illustrates a monitoring device that includes functionality for measuring blood pressure, SpO2, and ECG simultaneously, in accordance with some embodiments of the present disclosure.

FIG. 2A illustrates the monitoring device 120. As shown in FIG. 2A, the monitoring device 120 may comprise sensors 125A and 125B, each of which may include pulse oximetry/photoplethysmogram (PPG) and ECG functionality to measure a set of physiological parameters of a user including blood pressure, SpO2, and ECG during a single interaction with the monitoring device 120. The monitoring device 120 may measure all (or any subset) of these parameters simultaneously and the interaction may take place over any time period sufficient to perform measurements of all three parameters (e.g., a 30 second interaction with the device). Each of the sensors 125 may comprise an electrode 127, which may be comprised of any appropriate material and may be implemented in any appropriate shape. In one example, the electrodes 127 may each be comprised of conductive metal (e.g., stainless steel) that is circular in shape and attached to the exterior surface of the monitoring device 120. In another example, the electrodes 127 may each be comprised of conductive ink that is deposited in a square shape onto the exterior surface of the monitoring device 120. In the example of FIG. 2A, each electrode 127 may comprise a metal electrode that is square-shaped. As shown in FIG. 2A, each electrode 127 may include a circular aperture in the middle in which an optical sensor may be mounted. It should be noted that the location of the aperture indicated in FIG. 2A is for example purposes only, and the aperture may be positioned at any appropriate location on the electrode 127. The shape of the aperture may correspond to the shape of the optical sensor to be embedded therein. Each electrode 127 may have a respective optical sensor 129 embedded into its aperture. Each optical sensor 129 may include a light source and a light detector (both shown in FIG. 3), and may measure changes in blood volume during a cardiac cycle by illuminating the skin using the light source, and measuring changes in light absorption using the light detector (i.e., performing a PPG) as discussed in further herein. In some embodiments, only a first sensor 125 (e.g., 125A) may include an electrode 127 and an optical sensor 129, while the other sensor 125 (e.g., 125B) may only include an electrode 127 and the optical sensor 129 of the first sensor 125A may perform all PPG related functionality.

Figure 3:
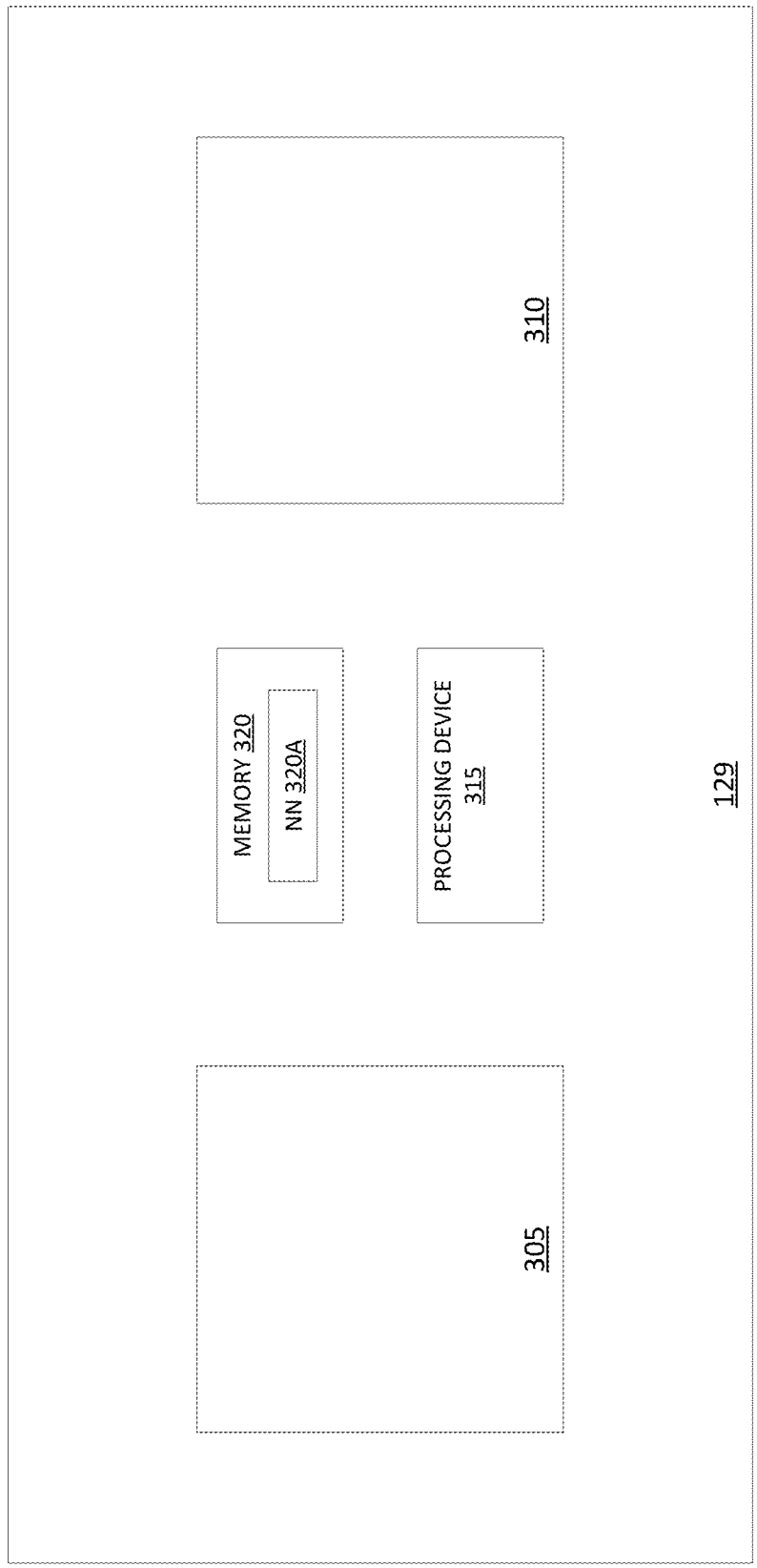
FIG. 3 illustrates an optical sensor, in accordance with some embodiments of the present disclosure.

FIG. 3 illustrates a hardware block diagram of an optical sensor 129 in accordance with some embodiments of the present disclosure. The optical sensor 129 may comprise a light source 305, a light detector 310, a processing device 315, and a memory 320. The light source 305 may comprise any appropriate light source such as a set of LEDs, and the light detector 310 may comprise any appropriate light detector such as a photodiode. The memory 320 may include a neural network (shown in FIG. 3 as NN 320A) that is trained to accurately detect/classify the blood pressure of a user within their demographic range based on PPG measurements and the user's demographic information. Thus, the optical sensor 129 may receive as one input, the demographic information (height, weight, age, and gender) of the user. The optical sensor 129 may receive the demographic information of a user at the beginning of each use (e.g., so that it may be used by different users) or may receive the demographic information of the user once during an initial use, and may be configured for use by that user only. The light source 305 may illuminate an appendage of the user (e.g., the user's finger) and the amount of light that is reflected from such illumination may be measured by the light detector 310 (i.e., a PPG measurement). The PPG measurement may indicate the change in light absorption across different wavelengths for the user's blood. In response to receiving the PPG measurements from the light detector 310, the processing device 315 may utilize the NN 320A to assess the blood pressure of the user based on the PPG measurement and the demographic information with clinical accuracy as discussed in further detail herein.

In some embodiments, the optical sensor 129 may be configured to perform a reflectance type PPG measurement where the light from the light source 305 does not travel all the way through the user's appendage (as opposed to a transmissive type PPG measurement where the light from the light source 305 does travel all the way through the user's appendage), and thus the optical sensor 129 may be implemented using a smaller form factor than that required by an optical sensor that is to perform a transmissive type PPG measurement. It should be noted that although the shape of each optical sensor 129 is illustrated in FIG. 2A as circular, this is for example purposes only and each optical sensor 129 (and the aperture in the corresponding electrode 127 where it will be embedded) may be implemented in any appropriate shape (e.g., square shaped).

The ability of an electrode 127 to measure an ECG is not affected by optics and the transmission and detection of reflected light by the corresponding optical sensor 129. As discussed hereinabove, the performance of an ECG relies on the conduction of electrical signals corresponding to activity of the user's heart through skin of user. As a result, the ability of the electrodes 127 to perform an ECG is indifferent to the presence of a respective optical sensor 129. However, for each sensor 125, the corresponding electrode 127 and optical sensor 129 may be subject to capacitive or inductive coupling that may pass between the electrode 127 and optical sensor 129. In some embodiments, the monitoring device 120 may include a conductive material (not shown) that separates the electrode 127 and optical sensor 129 of each sensor 125, providing isolation for each of the two sensors. For example, the aperture in which the optical sensor 125 is mounted may have a circular layer of conductive material that separates the electrode 127 from the optical sensor 129, and through which capacitive current may be dissipated. In other embodiments (e.g., where the optical sensor 129 is mounted adjacent to the electrode 127), the conductive material may be wrapped around the optical sensor 129 (or the portion of the optical sensor 129 that is in contact with the electrode 127).

Figure 2B:
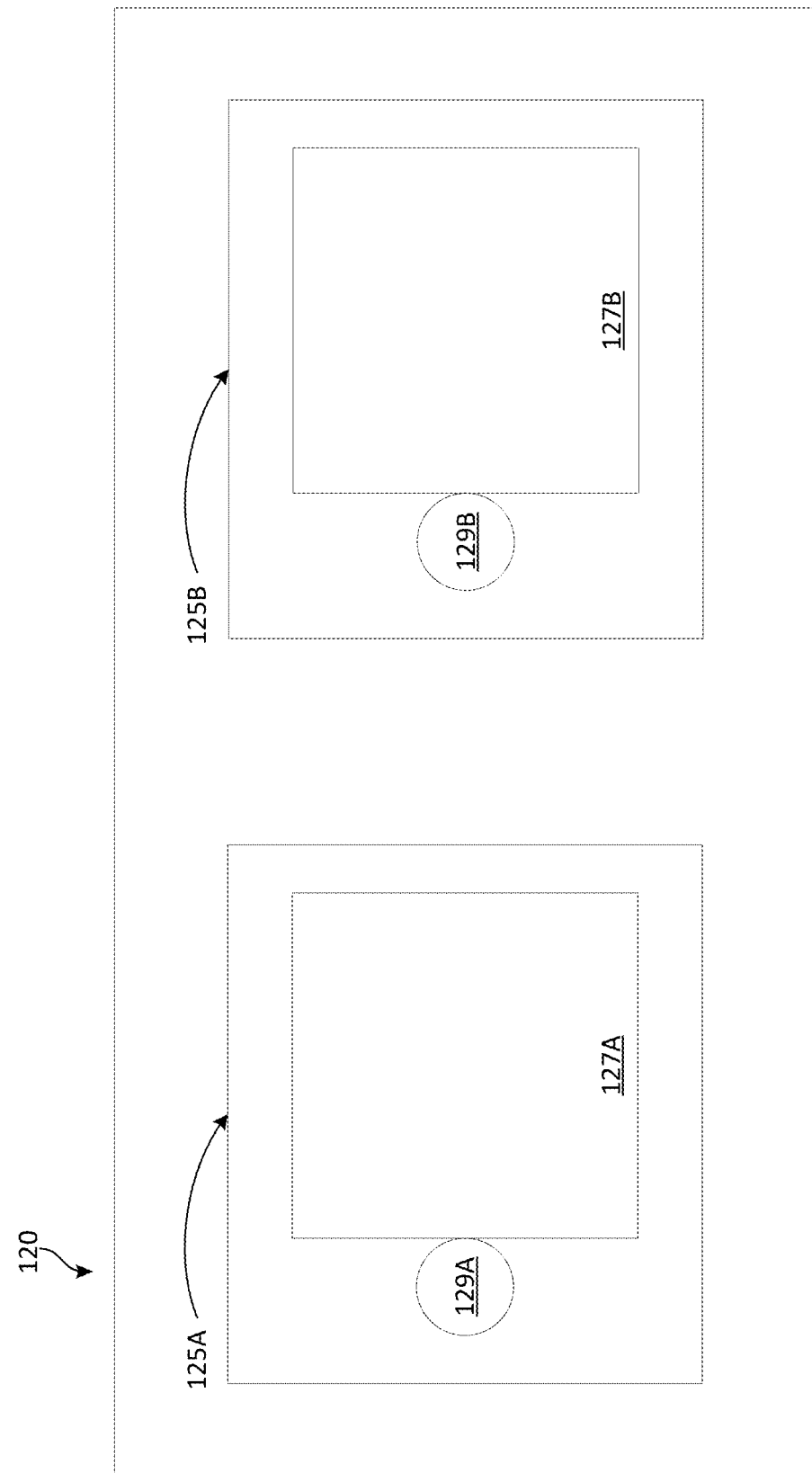
FIG. 2B illustrates a monitoring device that includes functionality for measuring blood pressure, SpO2, and ECG simultaneously, in accordance with some embodiments of the present disclosure.

In some embodiments, each sensor 125 may be implemented such that the surfaces of a respective electrode 127 and a respective optical sensor 129 may be flush with each other, while in other embodiments the surface of either a respective electrode 127 or a respective optical sensor 129 may protrude beyond the surface of the other. In some embodiments, the optical sensor 129 may not be embedded within a respective electrode 127, and instead may be implemented adjacent to or above/below a respective electrode 127. FIG. 2B illustrates the monitoring device 120 in an embodiment in which each optical sensor 129 is mounted adjacent to (e.g., side-by-side) a respective electrode 127.

The monitoring device 120 may be implemented in any manner (e.g., have any form factor) that allows for an electrical connection across the heart of the user that is sufficient to allow for accurate measuring of electrical signals corresponding to activity of the user's heart by the electrodes 127. In some embodiments, the monitoring device 120 may have a similar form factor as a handheld ECG monitor (such as the KardiaMobile® or KardiaMobile® 6L device from AliveCor® Inc., for example) comprising a smaller number of electrodes (e.g., 2 or 3 electrodes) relative to a device such as a Holter monitor. In the example of FIG. 2A or 2B, the electrodes 127 can be used to measure a single lead such as lead I (e.g., the voltage between the left arm and right arm) or lead II (e.g., the voltage between the left leg and right arm). In other examples where the monitoring device 120 comprises a third sensor 125C (shown in FIG. 2D), the electrodes 127 can be used to measure a subset of the leads described above. For example, the electrodes 127 can be used to measure e.g., lead I (e.g., the voltage between the left arm and right arm) contemporaneously with lead II (e.g., the voltage between the left leg and right arm), and lead I contemporaneously with lead V2 or another one of the chest leads such as V5. It should be noted that any other combination of leads is possible.

Figure 2C:
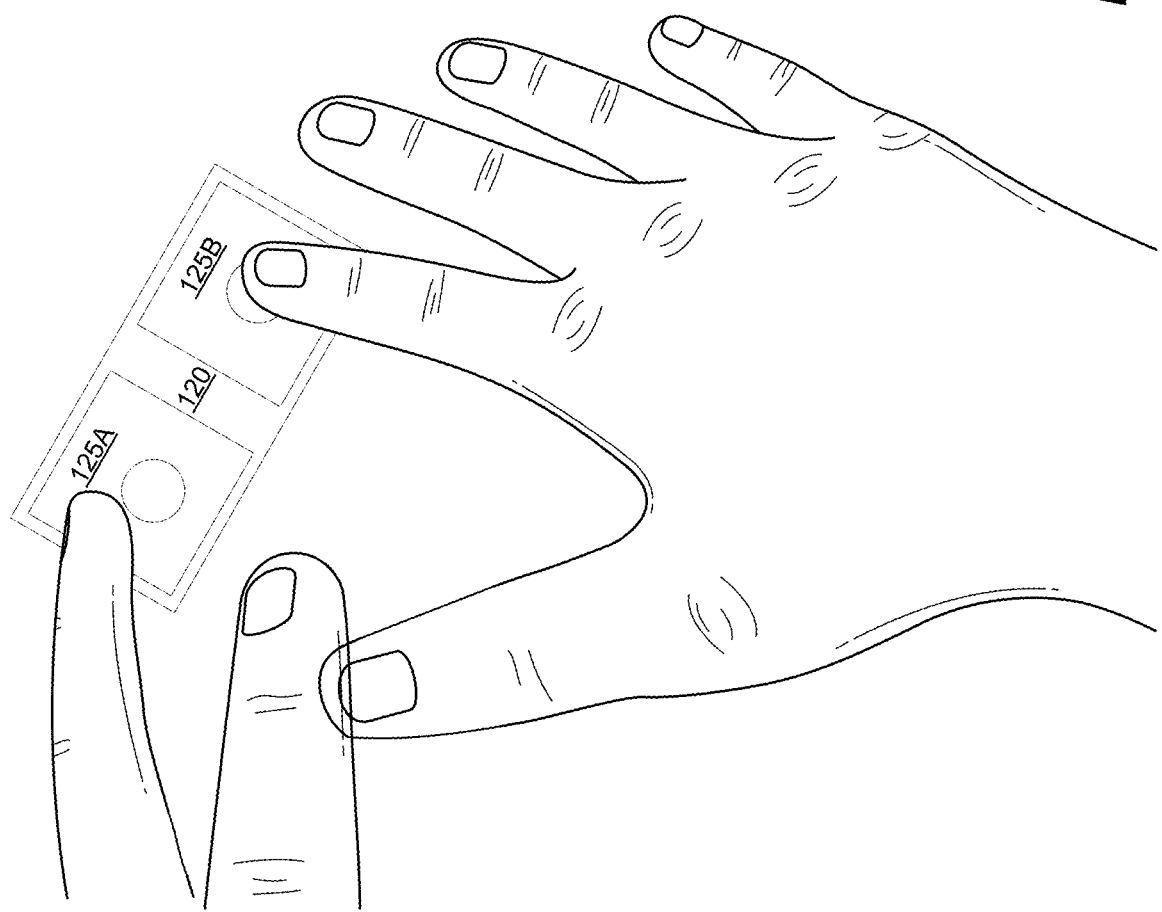
FIG. 2C illustrates the monitoring device of FIG. 2A in operation, in accordance with some embodiments of the present disclosure.
Figure 4:
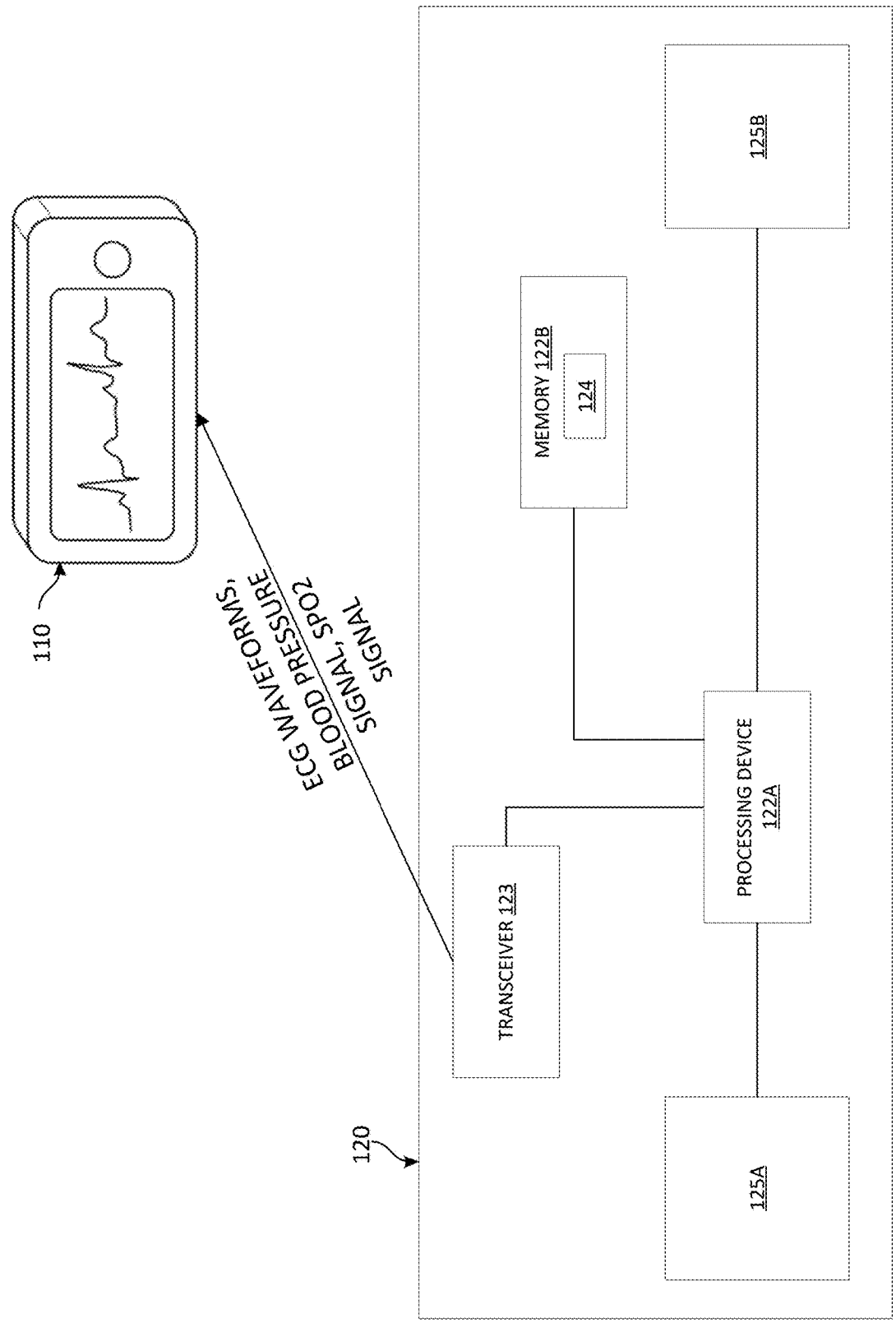
FIG. 4 illustrates a hardware block diagram of a monitoring device that includes functionality for measuring blood pressure, SpO2, and ECG simultaneously, in accordance with some embodiments of the present disclosure.

FIG. 2C illustrates the monitoring device 120 (as illustrated in FIG. 2A) in operation. Referring also to FIGS. 3 and 4, a user may contact the monitoring device 120 as shown in FIG. 2C so that each of their index fingers contacts a respective sensor 125. The processing device 122A may execute the monitoring module 124 to coordinate the functions of the sensors 125. More specifically, the electrodes 127 may perform an ECG of the user and obtain electrical signals corresponding to the electrical activity of the user's heart as discussed herein, while simultaneously, the optical sensors 129 perform a PPG in order to obtain the blood pressure and SpO2 (oxygen saturation) of the user. In some embodiments, the processing device 122A may instruct the electrodes 127 to perform an ECG of the user in response to detecting the user making contact with the sensors 125. The processing device 122A (executing the monitoring module 124) may process the electrical signals detected by the electrodes 127 to generate one or more ECG waveforms and store them in memory 122B and/or transmit them via transceiver 123 to e.g., computing device 110 for display and/or analysis. The processing device 122A (executing the monitoring module 124) may also process the blood pressure and SpO2 information received from the optical sensors 129 and store them in memory 122B and/or transmit them via transceiver 123 to e.g., computing device 110 for display and/or further analysis. Although illustrated as transmitting ECG waveforms, blood pressure information, and SpO2 information to computing device 110 for display/analysis, in some embodiments the monitoring device 120 may include a display (not shown) on which the ECG waveforms, blood pressure information, and SpO2 information can be displayed. In addition, in some embodiments, upon performing the ECG and PPG measurements, the monitoring device 120 may transmit the measured results of either or both of the PPG measurements to the computing device 110, which may perform the generation of the one or more ECG waveforms and the generation of the blood pressure and SpO2 signals (e.g., instead of the monitoring device 120).

The optical sensors 129 may derive the blood pressure and SpO2 of the user based on the manner in which blood absorbs different wavelengths of light. When the light source 305 of an optical sensor 129 transmits light through the user's appendage, the blood in the user's appendage will absorb more light from certain wavelengths of light than others. As a result, the blood pressure and SpO2 of the user are each based on a proportion of light wavelengths in reflected light that is detected by the light detector 310. More specifically, the ratios between certain light wavelengths that are detected by the light detector 310 may be used (e.g., by processing device 315) to determine and differentiate the blood pressure information and the SpO2 information. The ratio between wavelengths including e.g., red and infrared may be used to determine SpO2 because oxygenated blood absorbs more infrared light and allows more red light to pass through while deoxygenated hemoglobin allows more infrared light to pass through and absorbs more red light. Similarly, the ratio between e.g., green and yellow wavelengths may be used to determine blood pressure. As discussed above, upon parsing out the wavelengths of the detected light used to measure blood pressure, the processing device 315 may execute the NN 320A to assess the blood pressure of the user based on the ratio of the wavelengths of the detected light used to measure blood pressure and the demographic information with clinical accuracy. The processing device 315 may generate a blood pressure signal corresponding to the determined blood pressure and transmit the blood pressure signal to the processing device 122A. Upon parsing out the wavelengths of the detected light used to measure SpO2, the processing device 315 may assess the SpO2 of the user based on the ratio of the wavelengths of the detected light used to measure SpO2 using any appropriate techniques. The processing device 315 may generate an SpO2 signal corresponding to the determined SpO2 and transmit the SpO2 signal to the processing device 122A.

In some embodiments, only a first sensor 125A may be implemented with the NN 320A as shown in FIG. 3, while a second sensor 125B may be implemented as shown in FIG. 3 but without the NN 320A. In such embodiments, the first sensor 125A (via its corresponding optical sensor 129) may perform a PPG and analyze wavelengths corresponding to blood pressure so as to determine the blood pressure of the user and generate a blood pressure signal corresponding thereto. The second sensor 125B may (via its corresponding optical sensor 129) perform a PPG and analyze wavelengths corresponding to SpO2 so as to determine the SpO2 of the user and generate an SpO2 signal corresponding thereto. In this way, instead of each sensor 125 determining both blood pressure and SpO2 information, each sensor 125 may focus on a particular parameter to measure/analyze.

FIG. 2D illustrates the monitoring device 120 in operation in an embodiment where the monitoring device 120 includes a third sensor 125C. The third sensor 125C may be mounted on the underside of the monitoring device 120, and may include an electrode (not shown) but no optical sensor. A user may contact the monitoring device 120 as shown in FIG. 2D so that each of their index fingers contacts a respective sensor 125, while their left leg contacts sensor 125C. In this way, the electrodes 127 can be used to measure a subset of the leads described above instead of a single lead. For example, the electrodes 127 can be used to measure e.g., lead I (e.g., the voltage between the left arm and right arm) contemporaneously with lead II (e.g., the voltage between the left leg and right arm), and lead I contemporaneously with lead V2 or another one of the chest leads such as V5. It should be noted that any other combination of leads is possible. The electrode 127 of each sensor 125 may perform an ECG of the user, while the optical sensor 129 of sensors 125A and 125B may perform a PPG in order to obtain the blood pressure and SpO2 (oxygen saturation) of the user as discussed hereinabove. Although embodiments with 2 and 3 electrodes have been described herein, this is not a limitation and the monitoring device 120 may be implemented with any appropriate number of electrodes (e.g., additional sensors 125 that each have a respective electrode 127 and (optionally) optical sensor 129).

FIG. 4 illustrates a detailed hardware block diagram of the monitoring device 120 in accordance with some embodiments of the present disclosure. Memory 122B may include monitoring module 124 which may be executed by processing device 122A to coordinate the functions of the sensors 125. More specifically, the electrodes 127 may perform an ECG of the user and obtain ECG waveforms as discussed herein, while simultaneously, the optical sensors 129 perform a PPG in order to obtain the blood pressure and SpO2 (oxygen saturation) of the user. The processing device 122A (executing the monitoring module 124) may process the ECG waveforms and store them in memory 122B and/or transmit them e.g., to computing device 110 for display and/or analysis. The processing device 122A (executing the monitoring module 124) may also process the blood pressure and SpO2 information received from the optical sensors 129 and store them in memory 122B and/or transmit them via transceiver 123 to e.g., computing device 110 for display and/or analysis. In some embodiments, the monitoring device 120 may be implemented as a battery powered device so that it can be easily transported by the user and used in an on-demand fashion regardless of whether an electrical outlet or other external power supply is available. The monitoring device 120 may include a rechargeable battery or may include a battery housing (not shown) having a set of terminals into which replaceable batteries (E.g., AA, AAA, or D type batteries) may be inserted.

In some embodiments, the optical sensors 129 may perform a PPG in order to obtain blood pressure, heart rate, and SpO2 (oxygen saturation) signals (as well as any other appropriate signals) of the user on a continuous basis. In response to receiving blood pressure, heart rate, SpO2, or other signals from the optical sensors 129 that are outside of a predefined normal range, the processing device 122A may trigger performance of an ECG using the electrodes 127 to obtain further information regarding a possible health condition that the user is experiencing. For example, in response to receiving a heart rate signal that is outside of a normal range, the processing device 122A may use the electrodes 127 to perform an ECG. In another example, upon receiving blood pressure signals that are outside a normal range, the processing device 122A may determine that another blood pressure measurement using PPG signals combined with ECG signals is necessary to confirm the initial measurement. Thus, the processing device 122A may receive a first ECG reading from the electrodes 127 and simultaneously receive a first PPG from optical sensors 129. The processing device 122A may then receive a second ECG reading from the electrodes 127 and simultaneously receive a second PPG from the optical sensors 129 and generate an average ECG reading from the first and second ECG readings. The processing device 122A may determine a differential pulse arrival time based on the average ECG reading and the first and second PPGs and determine the blood pressure of the user based on the differential pulse arrival time.

In some embodiments, the monitoring device 120 may be in the form of a smartphone, or a wearable device such as a smart watch. In some embodiments, the monitoring device 120 may be a handheld sensor coupled to the computing device 110 as part of an intermediate protective case/adapter. For example, the monitoring device 120 may be removably coupled to the computing device 110 and may comprise a cover for covering the computing device 110, such as a tablet computer case or a smartphone case or cover. In this manner, the monitoring device 120 may not need to be replaced as the user replaces or upgrades his or her computing device 110. That is, the same monitoring device 120 may be used by the user for the different computing devices 110 the user may have.

Figure 5A:
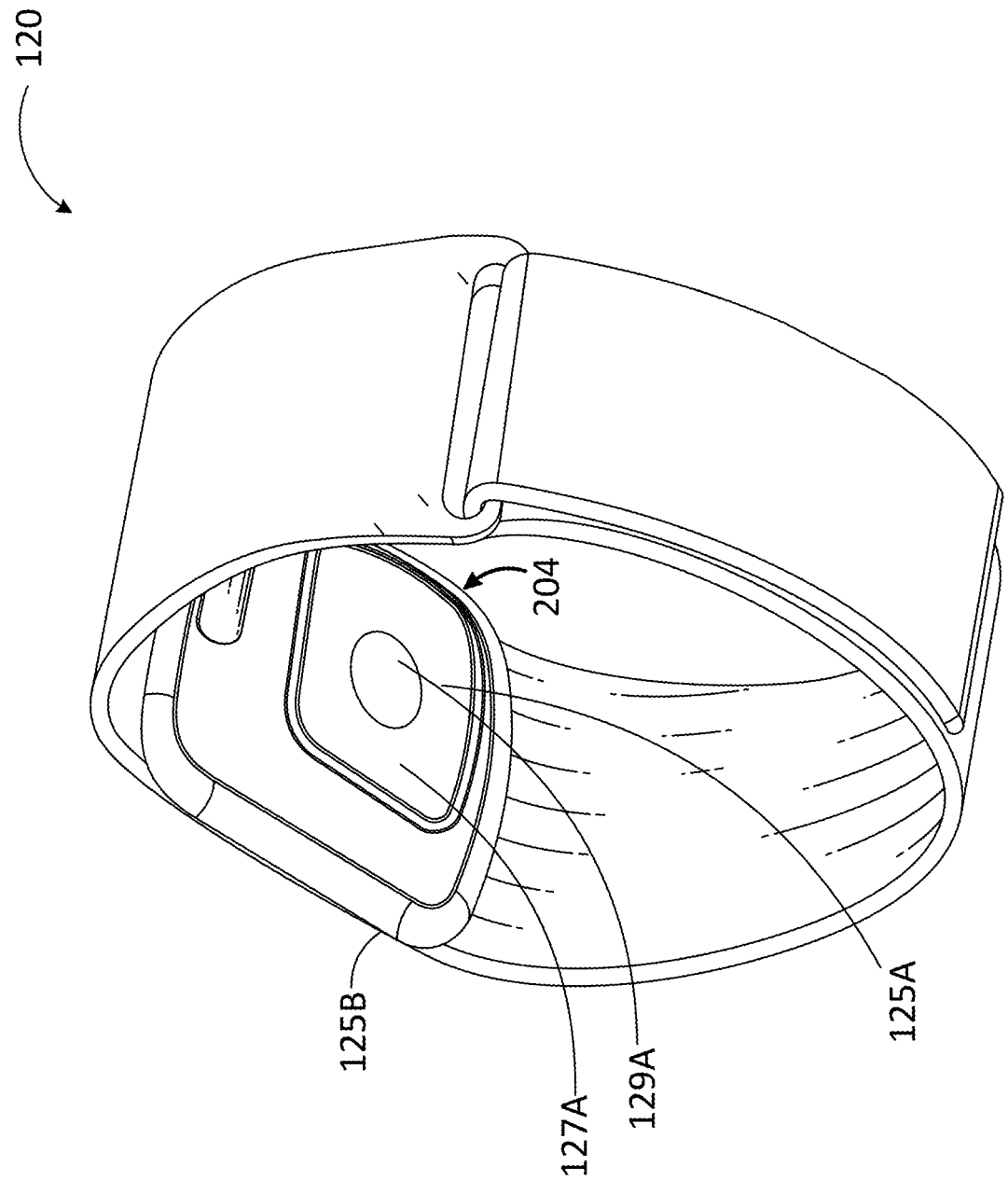
FIG. 5A illustrates a monitoring device that includes functionality for measuring blood pressure, SpO2, and ECG simultaneously implemented as a wearable device, in accordance with some embodiments of the present disclosure.
Figure 5B:
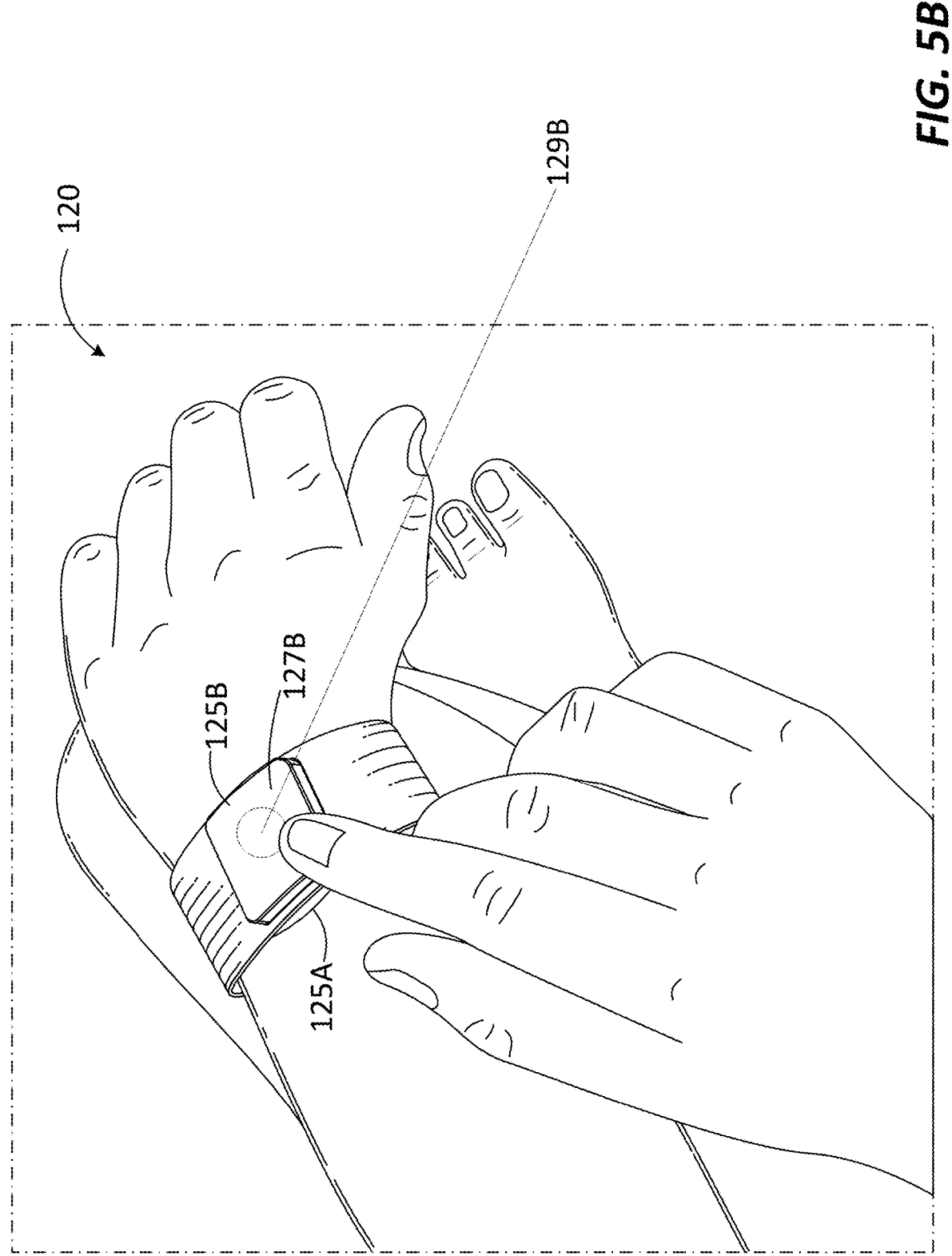
FIG. 5B illustrates a monitoring device that includes functionality for measuring blood pressure, SpO2, and ECG simultaneously implemented as a wearable device, in accordance with some embodiments of the present disclosure.

FIGS. 5A and 5B illustrate the monitoring device 120 in an embodiment where the monitoring device 120 is implemented as a wearable watch. As can be seen, the first sensor 125A may be located on an underside of the watch face while the second sensor 125B may be located on top of the watch face. When the user wears the monitoring device 120, the sensor 125A may already be contacting their left arm, and the user may contact the sensor 125B as shown in FIG. 5B. In this way, a single lead ECG can be taken by the electrodes 127 while the optical sensors 129 perform a PPG and obtain the blood pressure and SpO2 measurements as described in further detail hereinabove.

Figure 6:
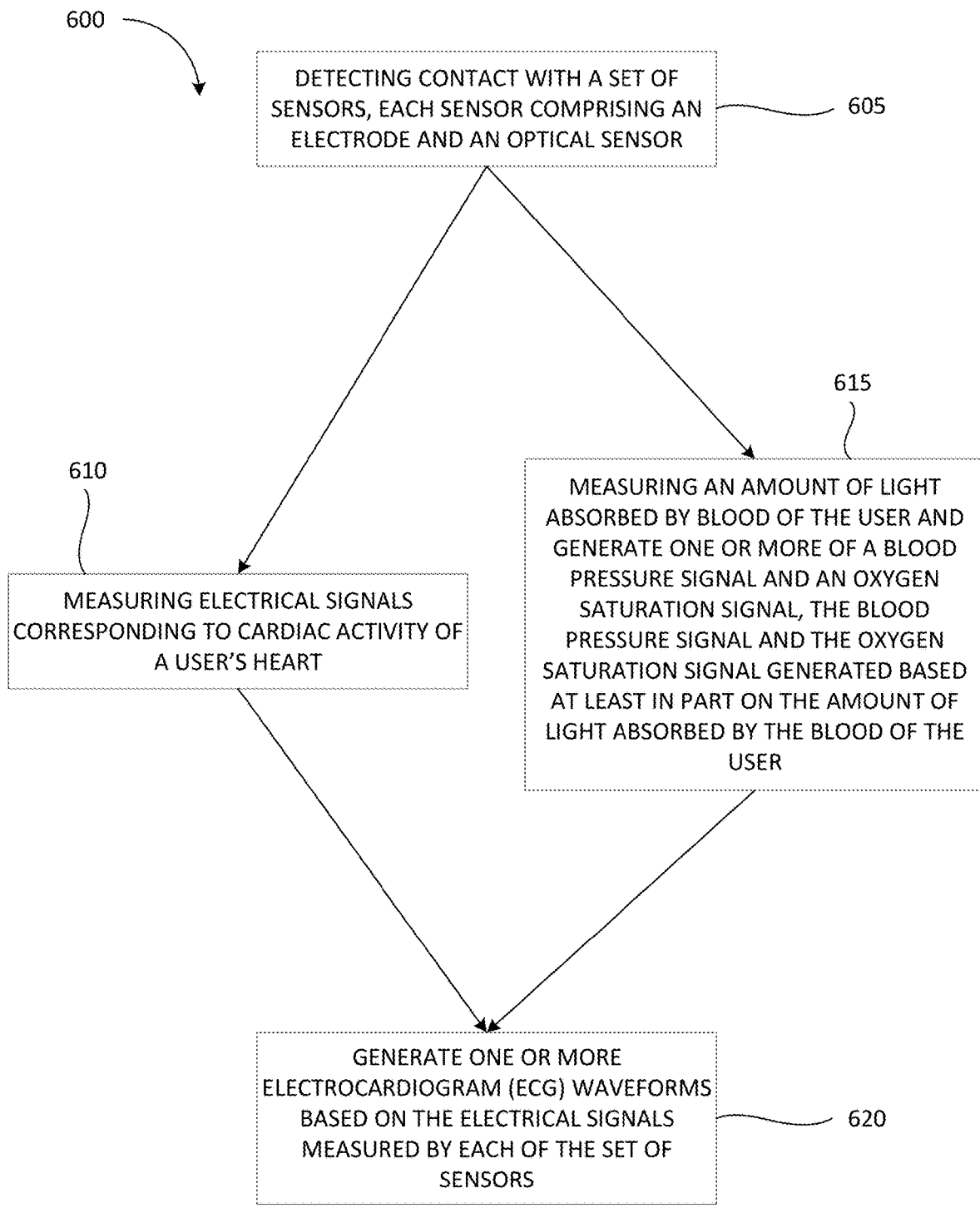
FIG. 6 is a flow diagram of a method for simultaneously measuring blood pressure, SpO2, and ECG using a handheld monitoring device, in accordance with some embodiments of the present disclosure.

FIG. 6 is a flow diagram of a method 600 for measuring blood pressure, SpO2, and ECG information simultaneously using a handheld device, in accordance with some embodiments of the present disclosure. Method 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 600 may be performed by monitoring device 120 as illustrated in FIGS. 2A and 4).

Referring simultaneously to FIGS. 2A, 2C, 3, and 4, a user may contact the monitoring device 120 as shown in FIG. 2C so that each of their index fingers contacts a respective sensor 125. At block 605, the processing device 122A may detect that the user has made contact with the sensors 125. The processing device 122A may execute the monitoring module 124 to coordinate the functions of the sensors 125. More specifically, at block 610, in response to the user contacting the sensors 125 as shown in FIG. 2C, the processing device 122A may instruct the electrodes 127 to perform an ECG of the user and obtain electrical signals corresponding to the electrical activity of the user's heart as discussed herein. At block 615, the processing device 112A may simultaneously instruct the optical sensors 129 to perform a PPG in order to obtain the blood pressure and SpO2 (oxygen saturation) of the user. The optical sensors 129 may derive the blood pressure and SpO2 of the user based on the manner in which blood absorbs different wavelengths of light. When the light source 305 of an optical sensor 129 transmits light through the user's appendage, the blood in the user's appendage will absorb more light from certain wavelengths of light than others. As a result, the blood pressure and SpO2 of the user are each based on a proportion of light wavelengths in reflected light that is detected by the light detector 310. More specifically, the ratios between certain light wavelengths that are detected by the light detector 310 may be used (e.g., by processing device 315) to determine and differentiate between blood pressure components of the PPG and SpO2 components of the PPG. The ratio between wavelengths including e.g., red and infrared may be used to determine SpO2, while the ratio between e.g., green and yellow wavelengths may be used to determine blood pressure, for example. As discussed above, upon parsing out the wavelengths of the detected light used for measuring the blood pressure, the processing device 315 may execute the NN 320A to assess the blood pressure of the user based on the ratio between e.g., green and yellow wavelengths in the detected light and the demographic information with clinical accuracy. The processing device 315 may generate a blood pressure signal corresponding to the determined blood pressure and transmit the blood pressure signal to the processing device 122A. Upon parsing out the wavelengths of the detected light used for measuring the SpO2, the processing device 315 may assess the SpO2 of the user based on the ratio between e.g., red and infrared wavelengths in the detected light. The processing device 315 may generate an SpO2 signal corresponding to the determined SpO2 and transmit the SpO2 signal to the processing device 122A.

At block 620, the processing device 122A (executing the monitoring module 124) may process the electrical signals detected by the electrodes 127 to generate one or more ECG waveforms and store them in memory 122B and/or transmit them via transceiver 123 to e.g., computing device 110 for display and/or analysis. The processing device 122A (executing the monitoring module 124) may also process the blood pressure and SpO2 information received from the optical sensors 129 and store them in memory 122B and/or transmit them via transceiver 123 to e.g., computing device 110 for display and/or analysis.

Figure 7:
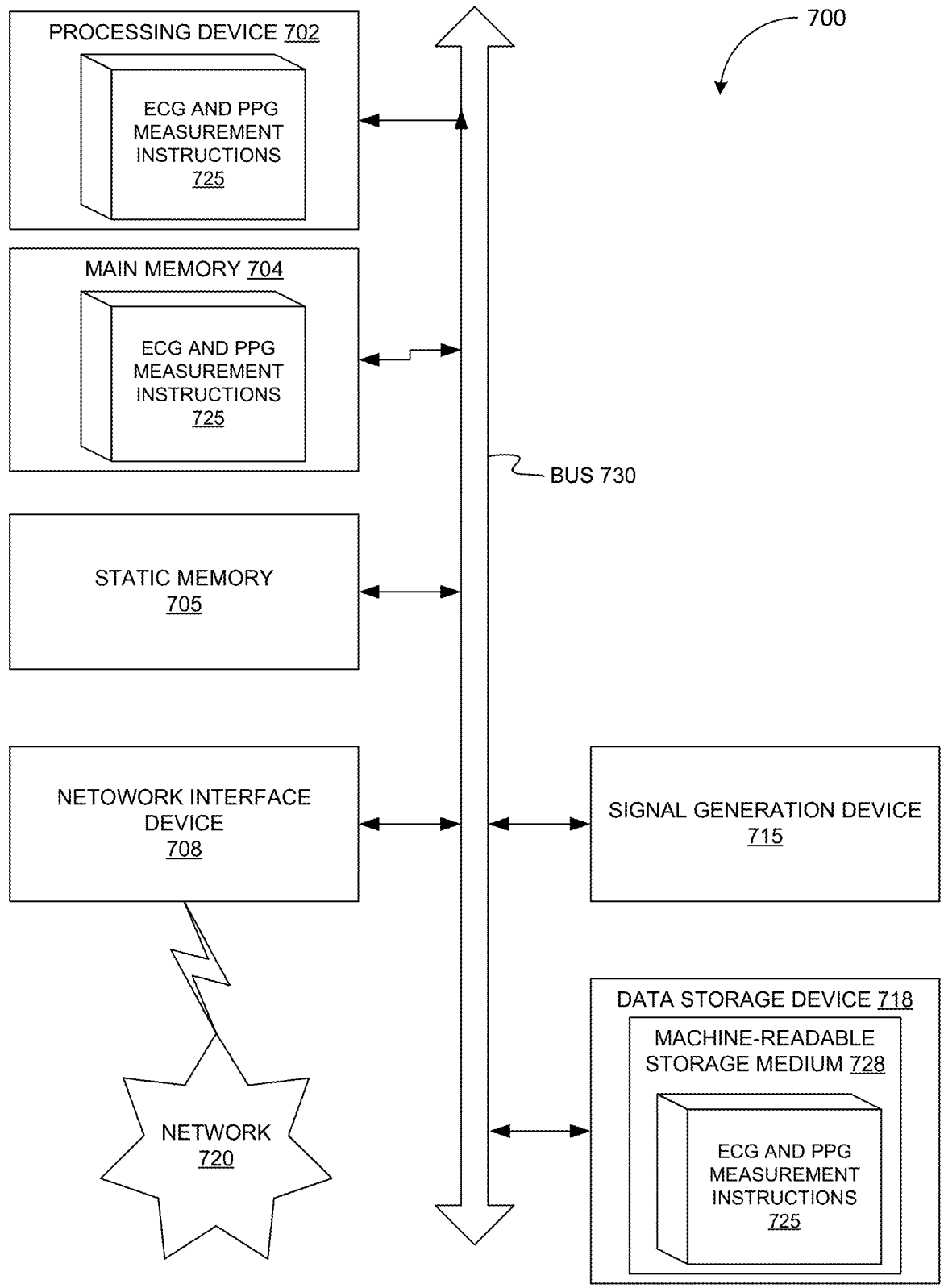
FIG. 7 is a block diagram of an example computing device that may perform one or more of the operations described herein, in accordance with some embodiments of the present disclosure.

FIG. 7 illustrates a diagrammatic representation of a machine in the example form of a computer system 700 within which a set of instructions, for causing the machine to perform any one or more of the embodiments discussed herein.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 700 may be representative of a server.

The exemplary computer system 700 includes a processing device 702, a main memory 704 (e.g., read-only memory (ROM), flash memory, dynamic random access memory (DRAM), a static memory 707 (e.g., flash memory, static random access memory (SRAM), etc.), and a data storage device 718, which communicate with each other via a bus 730. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 717 (e.g., a speaker). In one embodiment, video display unit 710, alphanumeric input device 712, and cursor control device 714 may be combined into a single component or device (e.g., an LCD touch screen).

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute ECG and PPG measurement instructions 725, for performing the operations and steps discussed herein.

The data storage device 715 may include a machine-readable storage medium 728, on which is stored one or more sets of ECG and PPG measurement instructions 725 (e.g., software) embodying any one or more of the methodologies of functions described herein. The ECG and PPG measurement instructions 725 may also reside, completely or at least partially, within the main memory 704 or within the processing device 702 during execution thereof by the computer system 700; the main memory 704 and the processing device 702 also constituting machine-readable storage media. The ECG and PPG measurement instructions 725 may further be transmitted or received over a network 720 via the network interface device 708.

While the machine-readable storage medium 728 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. An apparatus comprising:
a first sensor comprising a first electrode to measure electrical signals corresponding to cardiac activity of a user's heart;
a second sensor comprising:
a second electrode to measure electrical signals corresponding to cardiac activity of the user's heart; and
an optical sensor to measure an amount of light absorbed by blood of the user and generate one or more of a blood pressure signal and an oxygen saturation signal, the blood pressure signal and the oxygen saturation signal generated based at least in part on the amount of light absorbed by the blood of the user, wherein the amount of light absorbed by the blood of the user is measured concurrently with the electrical signals corresponding to cardiac activity of the user's heart, and wherein the second electrode includes an aperture within which the optical sensor is mounted; and
a processing device operatively coupled to the first and second sensors, the processing device to:
receive one or more of the blood pressure signal and the oxygen saturation signal from the second sensor;
receive the electrical signals measured by each of the first and second electrodes; and
generate one or more electrocardiogram (ECG) waveforms based on the electrical signals measured by each of the first and second sensors.

2. The apparatus of claim 1, wherein the optical sensor comprises:
a light source to project light at a body part of the user; and
a light detector to detect light reflected from the projection of light at the body part of the user, wherein the optical sensor measures the amount of light absorbed by the blood of the user from the light reflected from the projection of light at the body part of the user, and wherein the amount of light absorbed by the blood of the user comprises one or more wavelengths corresponding to the blood pressure of the user and one or more wavelengths corresponding to the oxygen saturation of the user.

3. The apparatus of claim 2, wherein the optical sensor further comprises:
a neural network that classifies the one or more wavelengths corresponding to the blood pressure of the user based on demographic information of the user to generate the blood pressure signal.

4. The apparatus of claim 3, wherein the demographic information includes a height, weight, age, and gender of the user.

5. The apparatus of claim 1, wherein the optical sensor is mounted adjacent to the second electrode within the second sensor.

6. The apparatus of claim 1, wherein the first sensor further comprises a second optical sensor to measure an amount of light absorbed by blood of the user, and wherein the first sensor is to generate the blood pressure signal and the second sensor is to generate the oxygen saturation signal.

7. The apparatus of claim 1, wherein the first and second sensors measure a single-lead ECG of the user so that the processing device generates a single ECG waveform based on the electrical signals measured by each of the first and second sensors.

8. The apparatus of claim 1, further comprising:
a transceiver to transmit the one or more ECG waveforms as well as the blood pressure and oxygen saturation signals to a computing device.

9. The apparatus of claim 1, further comprising:
a display to display the one or more electrocardiogram (ECG) waveforms and the one or
more of the blood pressure signal and the oxygen saturation signal.

10. The apparatus of claim 1, wherein the optical sensor is further to generate a heart rate signal based at least in part on the amount of light absorbed by the blood of the user.

11. The apparatus of claim 1, wherein the processing device is further to:
continuously measure blood pressure and oxygen saturation of the user using the optical sensor; and
in response to detecting that the blood pressure or the oxygen saturation of the user is outside a predefined normal range, performing an ECG measurement using the first and second electrodes.

12. A system comprising:
a computing device; and
a monitoring device comprising:
a first sensor comprising a first electrode to measure electrical signals corresponding to cardiac activity of a user's heart; and
a second sensor comprising:
a second electrode to measure the electrical signals corresponding to cardiac activity of a user's heart; and
an optical sensor to measure an amount of light absorbed by blood of the user and generate one or more of a blood pressure signal and an oxygen saturation signal, the blood pressure signal and the oxygen saturation signal generated based at least in part on the amount of light absorbed by the blood of the user, wherein the amount of light absorbed by the blood of the user is measured concurrently with the electrical signals corresponding to cardiac activity of the user's heart, and wherein the second electrode includes an aperture within which the optical sensor is mounted; and
a processing device operatively coupled to the first and second sensors, the processing device to:

receive one or more of the blood pressure signal and the oxygen saturation signal from the second sensor;

receive the electrical signals measured by each of the first and second electrodes; and generate one or more electrocardiogram (ECG) waveforms based on the electrical signals measured by each of the first and second sensors; and transmit the one or more ECG waveforms and the one or more of the blood pressure and the oxygen saturation signals to the computing device.

13. The system of claim 12, wherein the optical sensor comprises:

a light source to project light at a body part of the user; and a light detector to detect light reflected from the projection of light at the body part of the user, wherein the optical sensor measures the amount of light absorbed by the blood of the user from the light reflected from the projection of light at the body part of the user, and wherein the amount of light absorbed by the blood of the user comprises one or more wavelengths corresponding to the blood pressure of the user and one or more wavelengths corresponding to the oxygen saturation of the user.

14. The system of claim 13, wherein the optical sensor further comprises:

a neural network that classifies the one or more wavelengths corresponding to the blood pressure of the user based on demographic information of the user to generate the blood pressure signal.

15. The system of claim 14, wherein the demographic information includes a height, weight, age, and gender of the user.

16. The system of claim 12, wherein the optical sensor is mounted adjacent to the second electrode within the second sensor.

17. The system of claim 12, wherein the first sensor further comprises a second optical sensor to measure an amount of light absorbed by blood of the user, and wherein the first sensor is to generate the blood pressure signal and the second sensor is to generate the oxygen saturation signal.

18. The system of claim 12, wherein the first and second sensors measure a single-lead ECG of the user so that the processing device generates a single ECG waveform based on the electrical signals measured by each of the first and second sensors.

19. The system of claim 12, wherein the monitoring device further comprises:

a transceiver via which the processor may transmit the one or more ECG waveforms and the blood pressure and the oxygen saturation signals to the computing device.

20. The system of claim 12, further comprising:

a display to display the one or more electrocardiogram (ECG) waveforms and the one or more of the blood pressure signal and the oxygen saturation signal.

21. The system of claim 12, wherein the optical sensor is further to generate a heart rate signal based at least in part on the amount of light absorbed by the blood of the user.

22. The system of claim 12, wherein the processing device is further to:

continuously measure blood pressure and oxygen saturation of the user using the optical sensor; and in response to detecting that the blood pressure or the oxygen saturation of the user is outside a predefined normal range, performing an ECG measurement using the first and second electrodes.

* * * * *